United States Patent
Choi (10) Patent No.: US 9,486,174 B2
(45) Date of Patent: Nov. 8, 2016

(54) APPARATUS AND METHOD FOR RECONSTRUCTING PANORAMIC X-RAY IMAGE

(71) Applicants: Vatech Co., Ltd., Gyeonggi-do (KR); Vatech Ewoo Holdings Co., Ltd., Gyeonggi-do (KR)

(72) Inventor: Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/401,716

(22) PCT Filed: May 16, 2013

(86) PCT No.: PCT/KR2013/004378
§ 371 (c)(1),
(2) Date: Nov. 17, 2014

(87) PCT Pub. No.: WO2013/172685
PCT Pub. Date: Nov. 21, 2013

(65) Prior Publication Data
US 2015/0117743 A1    Apr. 30, 2015

(30) Foreign Application Priority Data
May 16, 2012    (KR) .................. 10-2012-0051935

(51) Int. Cl.
*G06K 9/00*    (2006.01)
*A61B 6/14*    (2006.01)
(Continued)

(52) U.S. Cl.
CPC ............. *A61B 6/14* (2013.01); *A61B 6/466* (2013.01); *A61B 6/5223* (2013.01); *G06Q 50/24* (2013.01)

(58) Field of Classification Search
USPC ....... 382/100, 103, 128–132, 154, 162, 173, 382/181, 193, 199, 209, 219, 232, 254, 382/274–276, 284–294, 305, 312, 255; 345/419; 378/21, 4, 38, 11
See application file for complete search history.

(56) References Cited

U.S. PATENT DOCUMENTS

| 8,634,515 B2 | 1/2014 | Cho et al. |
| 8,693,624 B2 * | 4/2014 | Spartiotis ................ A61B 6/14 378/38 |

(Continued)

FOREIGN PATENT DOCUMENTS

| JP | 2008-086659 A | 4/2008 |
| JP | 2010-011910 A | 1/2010 |

(Continued)

*Primary Examiner* — Seyed Azarian
(74) *Attorney, Agent, or Firm* — IP Legal Services, LLC (57) ABSTRACT

The present invention provides an apparatus and method for reconstructing a panoramic X-ray image. The apparatus includes a storage unit for storing image data of multiple image layers; an image processing unit for determining a reference image layer among the multiple image layers, finding blocks that correspond to at least one block designated in the reference image layer from other image layers, selecting a clearest block by comparing image data of the corresponding blocks, and reconstructing the reference image layer by replacing the designated block in the reference image layer with the clearest block selected in any of the other image layers, if the selected block is not the same as the designated block in the reference image layer; and a display unit for displaying a panoramic image of the reconstructed reference image layer.

14 Claims, 7 Drawing Sheets

(51) Int. Cl.
*A61B 6/00* (2006.01)
*G06Q 50/24* (2012.01)

(56) References Cited

U.S. PATENT DOCUMENTS

| | | |
|---|---|---|
| 9,117,301 B2 | 8/2015 | Cho et al. |
| 2006/0203959 A1 | 9/2006 | Spartiotis et al. |
| 2008/0019477 A1 | 1/2008 | Spartiotis et al. |
| 2008/0063139 A1 | 3/2008 | Pantsar et al. |
| 2010/0142673 A1 | 6/2010 | Pantsar et al. |
| 2010/0208866 A1 | 8/2010 | Spartiotis et al. |
| 2010/0246761 A1 | 9/2010 | Pantsar et al. |
| 2011/0044520 A1* | 2/2011 | Nakai ............... A61B 6/032 382/131 |
| 2011/0103659 A1* | 5/2011 | Choi ............... G06F 19/321 382/128 |
| 2012/0039435 A1* | 2/2012 | Arai ............... A61B 6/06 378/11 |
| 2012/0092334 A1* | 4/2012 | Yoo ............... A61B 8/00 345/419 |
| 2012/0224762 A1* | 9/2012 | Choi ............... A61B 6/14 382/132 |
| 2013/0003921 A1 | 1/2013 | Spartiotis et al. |
| 2013/0329854 A1 | 12/2013 | Spartiotis et al. |
| 2015/0146853 A1 | 5/2015 | Spartiotis et al. |

FOREIGN PATENT DOCUMENTS

| | | |
|---|---|---|
| JP | 2010-148676 A | 7/2010 |
| KR | 10-2002-0072078 A | 9/2002 |
| KR | 10-2002-0083069 A | 11/2002 |
| KR | 10-2010-0090595 A | 8/2010 |
| KR | 10-2010-0119224 A | 11/2010 |
| KR | 10-2011-0048118 A | 5/2011 |

* cited by examiner

APPARATUS AND METHOD FOR RECONSTRUCTING PANORAMIC X-RAY IMAGE

CROSS REFERENCE TO RELATED APPLICATIONS

This application is a National Stage Patent Application of PCT International Patent Application No. PCT/KR2013/004378 (filed on May 16, 2013) under 35 U.S.C. §371, which claims priority to Korean Patent Application No. 10-2012-0051935 (filed on May 16, 2012), the teachings of which are incorporated herein in their entireties by reference.

TECHNICAL FIELD

The present invention relates generally to a technology for handling an image captured by panoramic X-ray imaging equipment, and more particularly to an apparatus and method for presenting an image captured by the panoramic imaging equipment on a screen of a user's digital display device.

BACKGROUND ART

A panoramic X-ray image is obtained by separately scanning individual sections of a human body, and combining the captured images into a single image. For creating a panoramic X-ray image, an X-ray source and a detector are moved based on an image focus trajectory determined based on the shape of a subject. For example, in case of a dental panoramic X-ray imaging apparatus, the X-ray source and detector may move taking into account an image focus trajectory determined based on the shape of a patient's dental arch and dental arrangement. Multiple image focus trajectories may be configured depending on gender, age, etc., but it is not easy to obtain an entirely clear panoramic image only from the determined image focus trajectory because the shape of the dental archs and dental arrangements are different from person to person.

DISCLOSURE

Technical Problem

Accordingly, the present invention has been made to solve the above problems occurring in the prior art, and an object of the present invention is to provide an image data providing apparatus that has a dedicated viewer to store and manage multiple panoramic images and present them, and which enables the user to select (or convert) all or a part of a particular image impossible to read due to a focus error in an area of interest in a patient into image data of image layers desired by the user, thereby providing more useful diagnostic information.

Another object of the present invention is to provide an image data providing apparatus that displays combined multi-focus image data generated by separating and recognizing image layer information of image data into a set of block units and combining the image data using the image layer information for a location of a selected block unit.

Technical Solution

Image data of a corresponding block is selected from among volume image data defined as a set of image data for multiple image layers, and correction of the selected data is performed for display.

Advantageous Effects

The present invention may be applied to any programs for showing panoramic images such as an image viewer used in diagnosis, program adopted in photographing and so on, and it is possible to show images after a change and to control the images. Further, in the present invention, an image can be stored using multiple panoramic images, and it is possible to move image layers freely after photographing by providing a viewer with which trajectories can be changed.

BEST MODE FOR CARRYING OUT THE INVENTION

In accordance with an aspect of the present invention, an apparatus for reconstructing a panoramic X-ray image is provided. The apparatus includes a storage unit for storing image data of multiple image layers; an image processing unit for determining a reference image layer among the multiple image layers, finding blocks that correspond to at least one block designated in the reference image layer from other image layers, selecting a clearest block by comparing image data of the corresponding blocks, and reconstructing the reference image layer by replacing the designated block in the reference image layer with the clearest block selected in any of the other image layers, if the selected block is not the same as the designated block in the reference image layer; and a display unit for displaying a panoramic image of the reconstructed reference image layer.

The reference image layer may be selected from among the multiple image layers. The reference image layer may be obtained by dividing the multiple image layers into multiple sections, selecting a clearest image layer for each section, and combining selected image layers from the multiple sections.

The storage unit may store location information of the block in advance.

The apparatus may further include a user input unit for designating locations and the number of the blocks.

In accordance with another aspect of the present invention, a method for reconstructing a panoramic X-ray image is provided. The method includes storing image data of multiple image layers; determining a reference image layer among the multiple image layers; finding blocks that correspond to at least one block designated in the reference image layer from other image layers; selecting a clearest block by comparing image data of the corresponding blocks; and reconstructing the reference image layer by replacing the designated block in the reference image layer with the clearest block selected in any of the other image layers, if the selected block is not the same as the designated block in the reference image layer.

The reference image layer may be selected from among the multiple image layers.

The reference image layer may be obtained by dividing the multiple image layers into multiple sections, selecting a clearest image layer for each section, and combining selected image layers from the multiple sections.

The method may further include: before finding blocks that correspond to at least one block designated in the reference image layer from other image layers, designating the block with pre-stored location information of the block.

The method may further include: after determining the reference image layer among the multiple image layers, receiving locations and the number of the blocks from a user.

EMBODIMENTS FOR CARRYING OUT THE INVENTION

Embodiments of the present invention will now be described with reference to accompanying drawings. Like numerals indicate like elements throughout the specification and drawings. Thus, repetitive descriptions thereof will be omitted. In the description of the present invention, if it is determined that a detailed description of commonly-used technologies or structures related to the invention may unnecessarily obscure the subject matter of the invention, the detailed description will be omitted.

Figure 1:
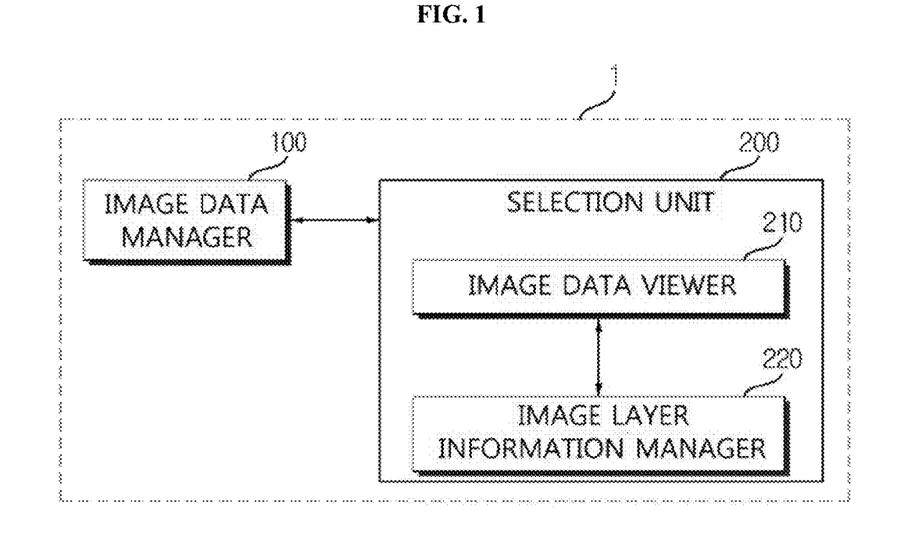
FIG. 1 is a block diagram of an image data providing apparatus, according to an embodiment of the present invention.

FIG. 1 is a block diagram of an image data providing apparatus 1 according to an embodiment of the present invention.

Referring to FIG. 1, the image data providing apparatus 1 may include an image data manager 100 for storing or managing image volume data and a selection unit 200 for selecting image data.

The image data manager 100 may receive, and store or manage volume image data reconstructed by combining image data of multiple image layers, which define a predetermined virtual plane such that a spatial plane constituted by focal points in capturing the image data corresponds to a trajectory plane in the space formed with interest regions.

The term image layer refers to a virtual segment or a virtual plane comprised of segments in a three dimensional (3D) space constituted by focal points for defining or specifying a location of an object (e.g., a dental arch including teeth in case of a dental image) to be captured. If the teeth actually intended to be captured correspond to a focal plane in a dental panoramic image, the resultant panoramic image obtained may be clear. However, since the dental arrangements are different from person to person, an actual dental layer of a patient is different from an image layer defined by a panoramic image obtaining system. Such inconsistency between the actual dental layer and the image layer hinders visibility of the resultant panoramic image.

Accordingly, in embodiments of the present invention, various image layers are predefined and used taking into account variety in spatial distribution of an object.

In an embodiment of the present invention, image data may be frame-based image data obtained by a panoramic image obtaining apparatus, or a reconstructed image data, e.g., a panoramic image as a final result.

In general, the panoramic image obtaining apparatus may include an X-ray source, a detector, and an image processing unit. The X-ray source irradiates X-rays while rotating around an object along certain trajectories. For example, the X-ray source may irradiate X-rays while rotating around the object along multiple image layer trajectories where an area of interest of the object is located. The detector has a certain area, and receives X-rays and obtains images along multiple image layer trajectories while moving with the X-ray source with the object located between the two. The image processing unit receives the images obtained from the detector and reconstructs the images for the image layer trajectories into a panoramic image for a final trajectory. In an embodiment of the present invention, the image layer trajectories include dental arch area by means of a capturer.

Figure 7:
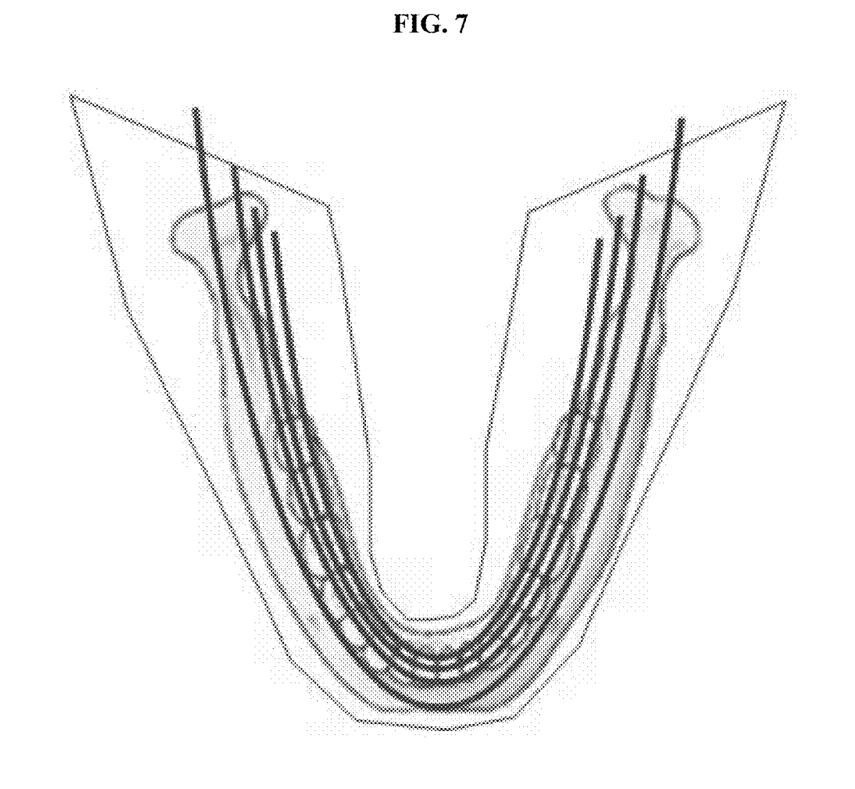
FIG. 7 a conceptual diagram illustrating multiple image layers.
Figure 8:
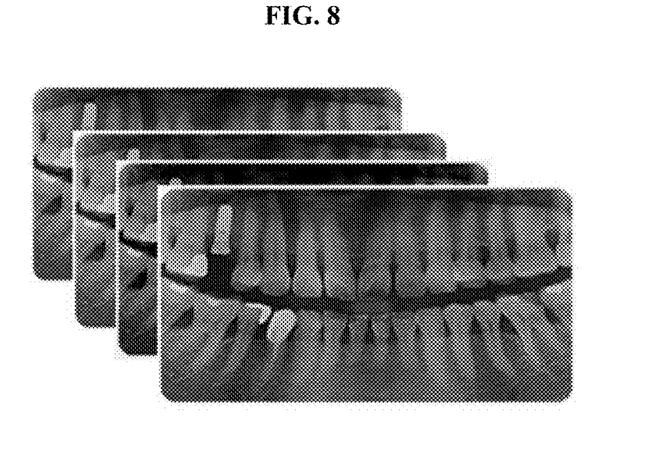
FIG. 8 shows panoramic images of multiple image layers.

Image information for each location of the object, which is output from an X-ray detector, may be multiple consecutive frame data. The image processing unit receives the image information obtained by the X-ray detector, i.e., the multi-frame data, and forms a panoramic image by overlapping the multi-frame data. Panoramic images of multiple image layers may be formed by varying the degree of overlap between frames. An example of variation of the degree of overlap may be the well-known Shift and Add (SAA). Accordingly, panoramic images of multiple image layers may be formed even with single panoramic image capturing. In the embodiment, the image layer may include the dental arch structure of a patient. FIG. 7 shows locations of multiple image layers in a dental arch, and FIG. 8 shows panoramic images of multiple image layers.

Volume image data is a set of image data reconstructed from image data of multiple image layers. The volume image data refers to a set of image data arranged in a different dimension by arranging pieces of data, resulting from combination of pieces of primitive image data into image data corresponding to an image layer, for the multiple image layers. The image layer refers to an image section in which image data is represented most clearly if a geometrical form of the object is identical to the image layer in making a match of the image data with a location of the object. In the embodiment, the image layer may include a dental arch structure of a patient. Reconstructing into a set of image data corresponding to multiple image layers includes selecting frame image data to overlap on a graphic unit basis, e.g., on a pixel basis, from among multiple pieces of frame image data, and setting the degree of overlap of the frame images based on the depth of the image layer in overlapping image data to build a panoramic image. The degree of overlap refers to an extent to which frame images overlap based on the depth of the image layer.

The volume image data may be stored in a storage device by arranging the volume image data for each image layer using image layer information of pieces of image data as identification values. Managing the volume image data may include reconstructing primitive image data into volume image data for multiple image layers, and specifically, searching for image data that corresponds to the image layer using the image layer information of the image data selected by the selection unit 200 and entering the image data into the selection unit 200.

The selection unit 200 receives a selection signal to select at least one of pieces of image data included in the volume image data using a first external input or a predetermined algorithm. The first external input includes a user input signal or an external input signal to select image data from outside of the image providing apparatus. In the embodiment, the user input signal may be one for selecting a clearest entire image or an image having a clearest area of interest to the user from among multiple pieces of image data (including reconstructed panoramic images). The predetermined algorithm may be one to select the image layer using a criterion predetermined in an internal process of the image providing apparatus. In a case that the area of interest is the dental arch of a patient, the algorithm may be one to recommend an average image layer using information about the patient's body, age, and gender. Such an algorithm is typically implemented in software. The image layer may also be an arbitrary image layer set as default.

The selection signal input to the selection unit may include an input signal to select image layers that correspond to the entire image data, or an input signal to select image layers for a part of the image data. If the selection signal is one to select a part of the image data, the selection of the part of the image data may be separately made from selection of the other parts of the image data. In the embodiment, the upper/lower dental arches in the anterior region have different depths, and thus the image layers may be adjusted separately; in a case that the surface of the teeth (crown region) and the root apex region (or root region) of all the teeth below the general posterior region have different image layers, the image layers may be separately selected.

In the embodiment, the selection unit 200 may include an image data viewer 210 for displaying image data selected by the selection unit 200 from the volume image data on the user screen, and an image layer information manager 220 for storing or managing information of image layers of the image data selected by the selection unit 200.

The image data viewer 210 displays the image data selected by the selection unit 200 on the user screen. The image data viewer 210 will be explained in more detail in connection with FIG. 2.

Figure 2:
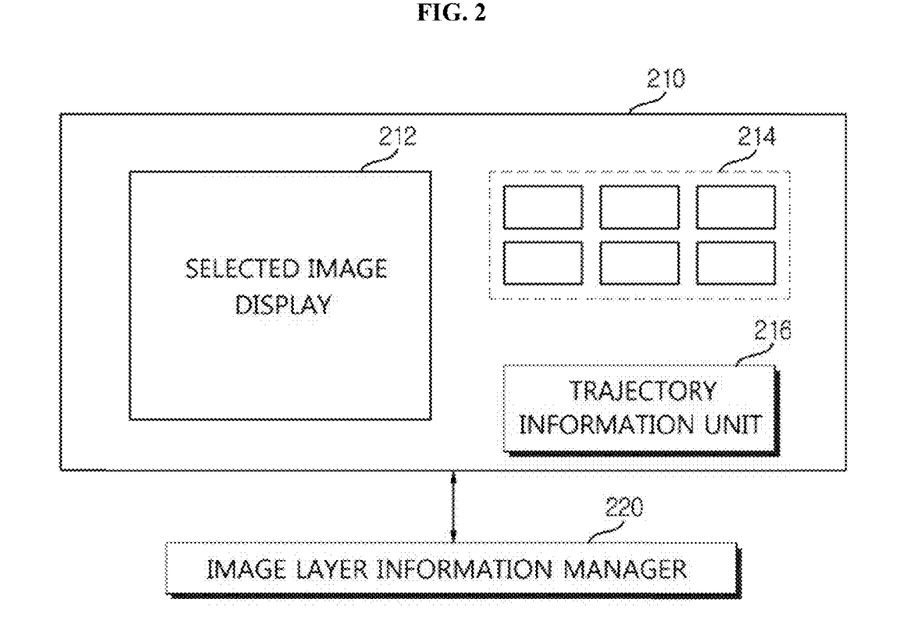
FIG. 2 is a detailed block diagram of an image data viewer, according to an embodiment of the present invention.

FIG. 2 is a detailed block diagram of the image data viewer 210, according to an embodiment of the present invention.

The image data viewer 210 may include a selected image display 212, a candidate image display 214, and a trajectory information unit 216.

The selected image display 212 is a part for virtually displaying the image data in the image data viewer 210. The selected image display 212 may display all of the image data for the entire image layer if the entire image layer is selected, or display partial image data for a partial image layer if the partial image layer of a part of the image data is selected. In the embodiment, if an area of interest in a patient is his/her teeth, the partial image layer may be the anterior region, more particularly, an image layer of the root apex in the anterior region. Further, the selected image display 212 may divide the image data for display into minimum units, i.e., into pixels or into a set of block units defined by a plurality of pixels including density independent pixels, scale independent pixels, etc., and manage the resultant units individually. If a second external input selects a particular block, coordinates or a range of the particular block may be recognized on the block unit basis. In the embodiment, the second external input may be made by the user holding the cursor or mouse pointer on a particular block including an area of interest intended to be clearly imaged, or clicking or dragging the particular block with the mouse. It may be also possible to select the particular block with the keyboard. Recognizing the location of the particular block may be recognizing a relative location of the selected particular block in the selected image display 212. If a section including the particular block is selected, a set of relative locations of the range of the particular block included in the section may be recognized. If the section is rectangular, a location of a block of the upper left corner of the section and the size of the section may be recognized.

In the embodiment, a location or section specified in the selected image display 212 may include the sinus, temporomandibular joint (TMJ), teeth having a disease or suspected of having a disease, etc. in the dental arch part of the patient. The sinus refers to a hole that leads from the inside of the nose into the skull. In the case of the sinus or TMJ, it generally requires additional image capturing because the image layer of a conventional dental panoramic image capturer is set to correspond to the patient's dental arrangement. However, in the embodiment of the present invention, the image data manager 100 may build an image focused on the sinus or TMJ upon reconstructing image data corresponding to multiple image layers, and image data that may represent a clear image for the part specified in the selected image display 212 may be displayed in the candidate image display 214.

The candidate image display 214 may display candidates of volume image data related to a particular location or particular section selected by the user using the image layer information. The candidate image display 214 may determine and display the candidates of the volume image data to be displayed in the particular location or section using the coordinate information or the range information recognized in the selected image display 212.

The candidates of the image data may be displayed in the form of thumbnails. Image data selected by the user in the candidate image display 214 according to a third external input may be displayed on a location or a section that corresponds to the coordinate information or range information recognized in the selected image display 212.

The candidate image display 214 may display candidates of the image data for clear image data that may correspond to the particular location or section in the form of thumbnails using the coordinate information or the range information regarding the particular block of the image data selected by the user according to the second external input recognized in the selected image display 212, and it is possible for the user to select clear image data for the particular location or range through the layout of the image data displayed in the form of thumbnails according to the third external input. The third external input may be a selection command generated by clicking or entering candidate image data required for the user among candidates of the image data with a mouse or keyboard. Thumbnails are used for preview, in which the layout of image data may be reviewed by reducing the entire image data and displaying the entire image data reduced on the screen. In addition to displaying images, such as thumbnails in parallel, there may be a coverflow method to display image data, in which pieces of image data are displayed to overlap each other and a piece of the image data may be selected in a way of turning pages of a book. Furthermore, the candidates of the image data may be displayed and selected through other previews.

The algorithm to select candidate image layers for a particular block according to the second external input may use the image layer information of image data displayed to correspond to neighboring coordinates or range to the coordinates or range of the particular block. The algorithm may select image data for the particular block of a neighboring image layer that clearly represents a neighboring block to the particular block. In the embodiment of the present invention, in the case that the area of interest is a dental arch, the geometrical shapes of the dental arches are different from person to person, but dental arch levels may be consecutive although there is a bit difference in depth and have an image layer having a depth close to an image layer of a neighboring level to the particular level. Accordingly, displaying volume image data that corresponds to image layers of image data neighboring to the coordinates or range recognized in the selected image display 212 may include displaying image data in a particular block that corresponds to image layers close to the image layers of image data displayed in the particular block within a certain range. Also, the algorithm may select an image layer estimated by considering a change in consecutive image layers of image data including left and right parts or upper and lower parts of the coordinates or region of the particular block. Image data that clearly represents the particular block may be image data of image layers having a certain range of depths including a midvalue taking into account the change in depths of image layers in consecutive locations or sections of the particular location or section including the left and right parts or upper and lower parts. In the embodiment, the depth refers to a distance between the panoramic image capturer and an image layer, meaning a relative extent of protrusion of the dental arch level. The volume image data displayed in the candidate image display 214 may further include image data selected by a predetermined algorithm in addition to the image data of neighboring image layers or the image data of an estimated image layer. The predetermined algorithm may determine candidate image data by analyzing spatial frequency components of the volume image data at a location that corresponds to the particular block according to the second external input, and the clearer an image is, the higher the frequencies in a particular high frequency band are that may be used. Frequency components of image data may represent distribution of contrasts at spatial locations in the image. In addition, an algorithm may be used that estimates candidate image data from which edge detection is best performed as clear data.

To display a substitute for a particular block of the image data selected in the candidate image display 214 according to the second external input, the selected image display 212 may display a corresponding block of candidate image data selected according to the third external input for a location or section that corresponds to the coordinates or range of the particular block. The corresponding block refers to partial candidate image data that corresponds to the particular block in the candidate image data selected according to the third external input. The corresponding block may be corrected for display. In the embodiment, correcting the corresponding block may include performing expansion correction or reduction correction on the size of the partial image data taking into account the image layer of the partial image data of the corresponding block and the image layer of the existing image data of the particular block. Furthermore, the correction may be performed by considering relations between the particular block and neighboring image data. In the embodiment, for any of the multiple image layers, the absolute area scanned by the capturing device through X-ray irradiation may be different depending on the depth of the image layer. The difference in scanned area may cause distortion of the size of an area of interest (e.g., the anterior region of the teeth) in the corresponding block as compared to an area of interest in image data displayed in a neighboring block to the particular block (e.g., teeth located around the anterior region). Accordingly, correction may be a process of reduction or expansion of the corresponding block using the share of the scanned area of X-rays.

The trajectory information unit 216 may display image layers for the image data displayed in the selected area display 212 as information about a trajectory plane in which an actual area of interest is displayed in 3D. Since the image data displayed in the selected image display 212 is represented as a plane image, it is hard to know where a particular location or section of the image data is located in the actual area of interest. Accordingly, in the embodiment of the present invention, if the user selects a particular location or section of the image data in the selected area display 212, it is possible to indicate where the location or section selected in the trajectory information unit is located in the actual dental arch level.

Figure 3:
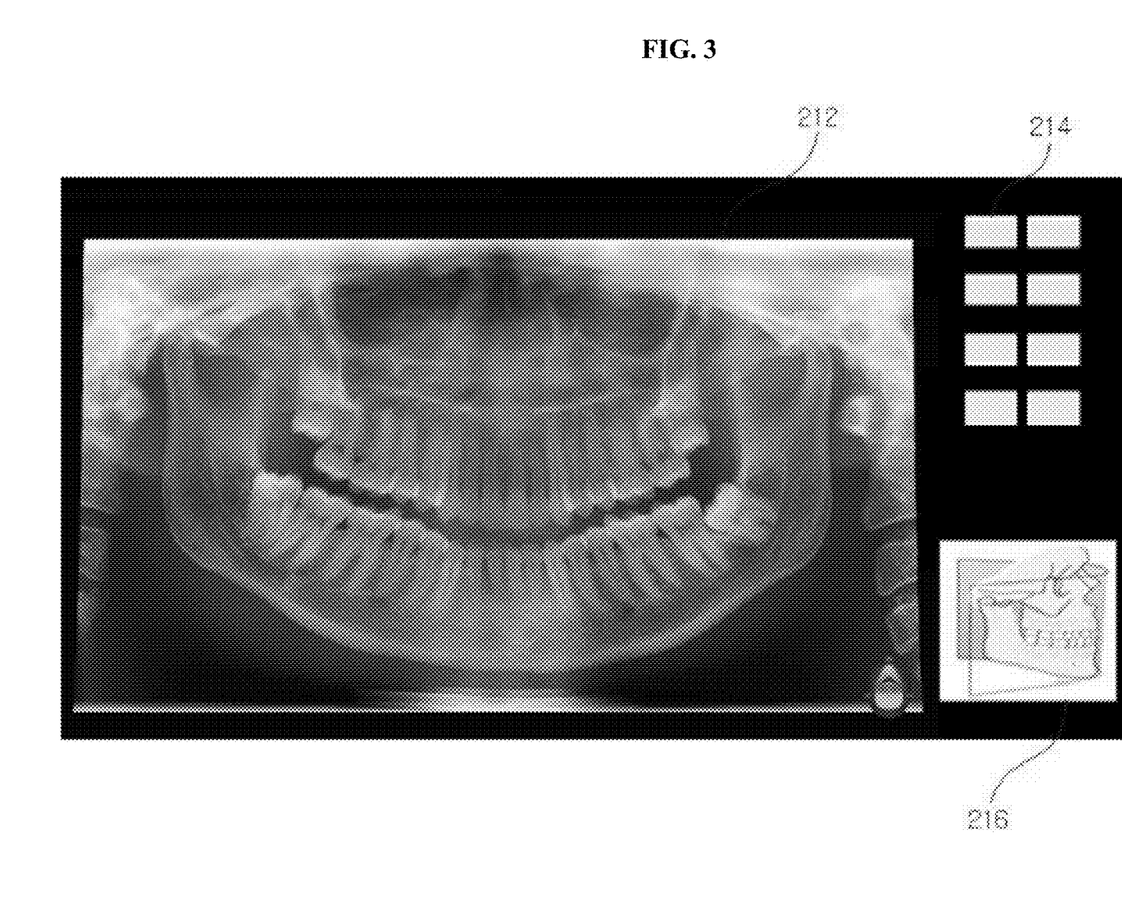
FIG. 3 shows an exemplary panoramic image data viewer for a dental arch, according to an embodiment of the present invention.

FIG. 3 shows an exemplary panoramic image data viewer for a dental arch according to an embodiment of the present invention. The selected image display 212 displays a panoramic image captured for a dental arch in an area of interest in a patient, and the candidate image display 214 displays candidate pieces of image data that clearly represent a particular block. The trajectory information unit 216 located in the lower left corner displays the dental arch of the patient in 3D.

Figure 4:
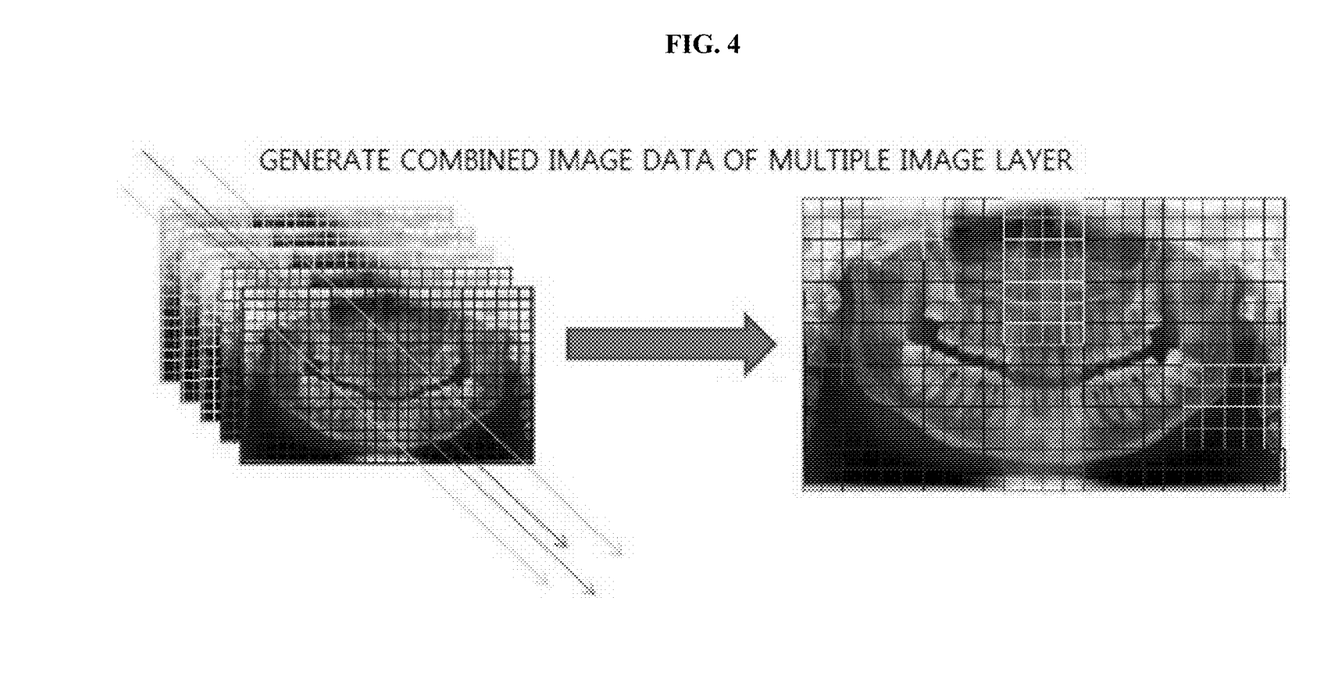
FIG. 4 shows exemplary panoramic image data for a dental arch, which is finally combined from multiple image layers, according to an embodiment of the present invention.

The image layer information manager 220 may store or manage selected image layer information of the selected image data. The selected image layer information may be image layer information of image data selected according to the third external input for selecting a clear image based on the location information of a particular block selected according to the second external input. In the embodiment, the selected image layer information may be an identification number of an image layer that most clearly represents the anterior region of the patient. In the embodiment, a panoramic image of the dental arch of the patient may be finally generated by combining clear partial pieces of image data that correspond to a particular location or particular section using the image layer information of the image data selected in the candidate image display 214. FIG. 4 shows an exemplary panoramic image data of a dental arch, finally combined from multiple image layers, according to an embodiment of the present invention. A panoramic image is shown, which is a combination of pieces of image data that clearly represent particular areas separated by different colors.

The selected image display 212 may display the final image data generated by combining pieces of image data selected by an external input including a user's selection or by a predetermined algorithm in respective locations or sections using the image layer information.

Figure 5:
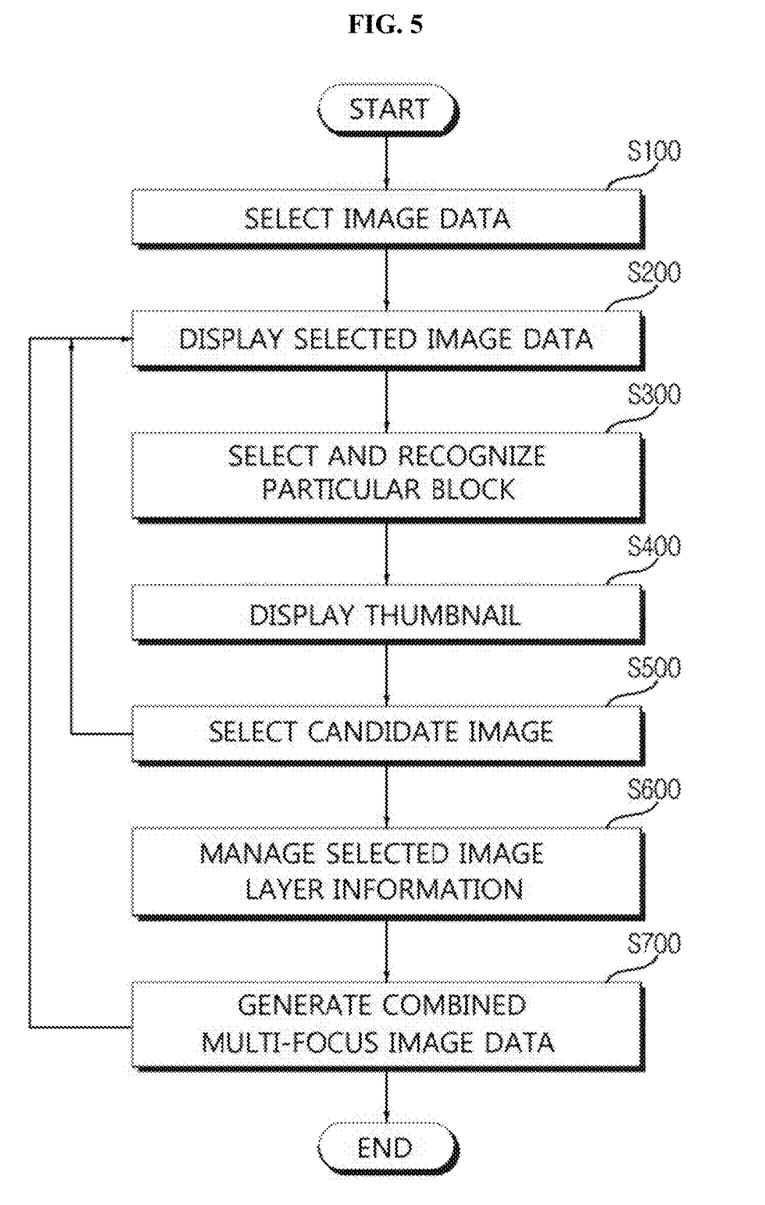
FIG. 5 is a flowchart illustrating a method for providing image data, according to an embodiment of the present invention.

FIG. 5 is a flowchart illustrating a method for providing image data, according to an embodiment of the present invention.

The method may include: selecting image data among volume image data, in operation S100; displaying the selected image data on the user screen, in operation S200; selecting at least one particular block of the displayed image data according to a second external input and recognizing location information of the selected particular block, in operation S300; displaying candidate pieces of image data using the recognized location information, in operation S400; selecting at least one of the candidate pieces of image data according to a third external input, in operation S500; storing or managing selected image layer information that defines image layer information of the image data selected according to the third external input, in operation S600; and generating combined multi-focus image data using the image layer information, in operation S700.

Selecting image data among volume image data in operation S100 may include selecting a piece of image data from the volume image data according to a first external input or a predetermined algorithm. The first external input includes a signal to select image data from outside of the image providing apparatus, including an input from the user. In the embodiment, the first external input may be a user's selection of an image layer to select clear image data. The predetermined algorithm may refer to a selection according to an internal process.

In operation S200, the image data selected in operation S100 may be displayed on the screen of a user's digital display device. Specifically, in operation S200 where the image data is displayed, it is preferable to separate the image data into minimum units, i.e., into pixels or into a set of block units defined by a plurality of pixels including density independent pixels, scale independent pixels, etc., and thus manage them individually. Once the particular location or particular section of the image data is specified according to the first external input or the predetermined algorithm, coordinates or a range of the specified location or section may be recognized on the graphical unit basis.

In operation S300, once the particular block of the displayed image data is selected according to the second external input, coordinates or a range of the particular block may be recognized on the aforementioned block unit basis.

In operation S400, candidate pieces of clear image data may be displayed corresponding to the particular location or section, using the coordinates or the range of the particular block of the image data selected by the user according to the second external input, which are recognized in S300. The candidate pieces of image data may include pieces of image data in the particular location or section that corresponds to image layers adjacent to an image layer of image data displayed to correspond to neighboring coordinates or neighboring range to the recognized coordinates or range. Furthermore, image data estimated taking into account a change in consecutive image layers of image data including left and right or upper and lower parts of the recognized coordinates or range may be image data of image layers having a certain range of depths including a mid-value by considering the change in depth of the image layers in a successive location or range including the left and right or upper and lower parts of the particular location or range.

It is also possible to display the candidate pieces of image data in the coverflow method, in which thumbnails or pieces of image data are displayed to overlap each other and a required piece of image data may be selected in a way of turning pages in a book. Furthermore, the candidate pieces of image data may be selected through other previews.

In operation S500, it is possible to select clear image data for a particular block through a layout of the image data displayed in thumbnails, according to the aforementioned third external input.

In operation S600, the image layer information of the candidate piece of image data selected as in operation S500 may be stored or managed as associated image layer information using the coordinate or range information recognized for the particular block.

In operation S700, pieces of image data selected according to the second and third external inputs for respective blocks may be combined into multi-focus image data using the image layer information.

Back in operation 300, the image layer information input in operation S500 may be used to display image data corresponding to the image layer. In operation 300, the panoramic image data, i.e., the combined multi-focus image data generated in operation S700 may also be displayed.

The apparatus and method for providing image data according to the embodiments of the present invention may be embodied as computer-readable codes on a computer-readable recording medium. The computer-readable recording medium is any data storage device that can store data which can be thereafter read by a computer system.

For example, the computer-readable recording medium may include a Read Only Memory (ROM), a Random Access Memory (RAM), a Compact Disc ROM (CD-ROM), a magnetic tape, a floppy disk, an optical data storage device, etc., and the computer readable recording medium can also be distributed over network coupled computer systems so that the computer readable code is stored and executed in a distributed fashion. Furthermore, functional programs, codes and code segments to implement the embodiments of the present invention may be readily inferred by programmers in the art.

Figure 6:
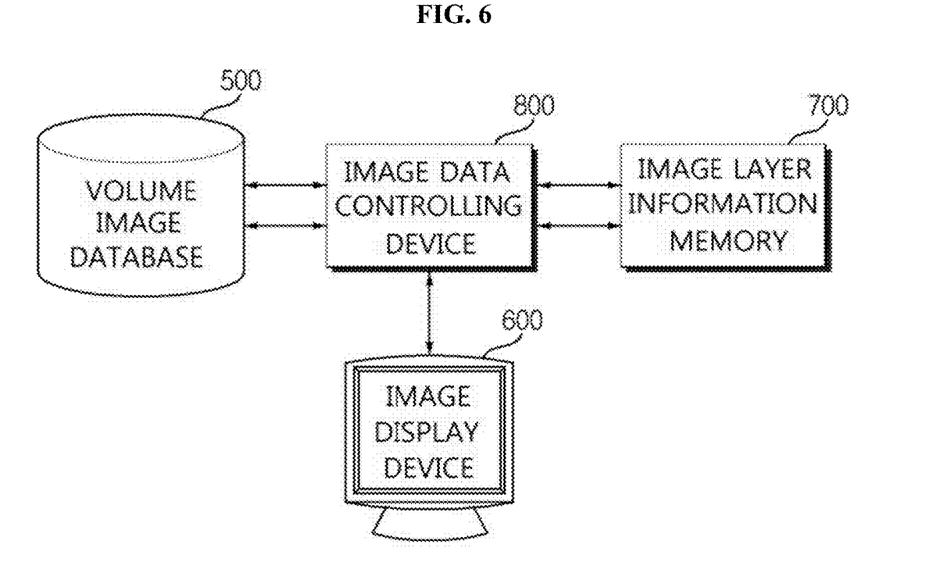
FIG. 6 is a schematic diagram of an apparatus for forming a panoramic X-ray image, according to an embodiment of the present invention.

FIG. 6 is a block diagram of a panoramic X-ray image processing and displaying apparatus, according to an embodiment of the present invention.

The apparatus may include a volume image database 500 for storing volume image data in accordance with embodiments of the present invention, an image display device 600 for receiving and displaying at least a piece of the image data stored in the volume image database 500, an image layer information memory 700 for storing or managing image layer information for image data requested for change, and an image data controlling device 800 for changing image data.

The volume image database 500 may store and manage pieces of volume image data that refer to a set of pieces of image data for multiple image layers, as described above.

The image display device 600 may display image data input from the image data controlling device 800. The image data controlling device 800 receives image data in the volume image database 500 using information including a change or selection of an image layer, which is stored in the image layer information memory 700, and forwards the image data to the image display device 600.

The image layer information memory 700 may store image layer information for image data requested for change, if there is a request for change of the entire or a part of an image layer of the image data by means of the image data displayed in the image display device 600 according to the third external input. The request for change may be a request for selection of image data that clearly represents an area of interest for a particular block according to the second external input as described above.

The image controlling device 800 may receive image layer information from the image layer information memory 700, and change the entire or a part of the image data displayed on the screen to the entire or a part of image data that corresponds to the received image layer information.

Figure 9:
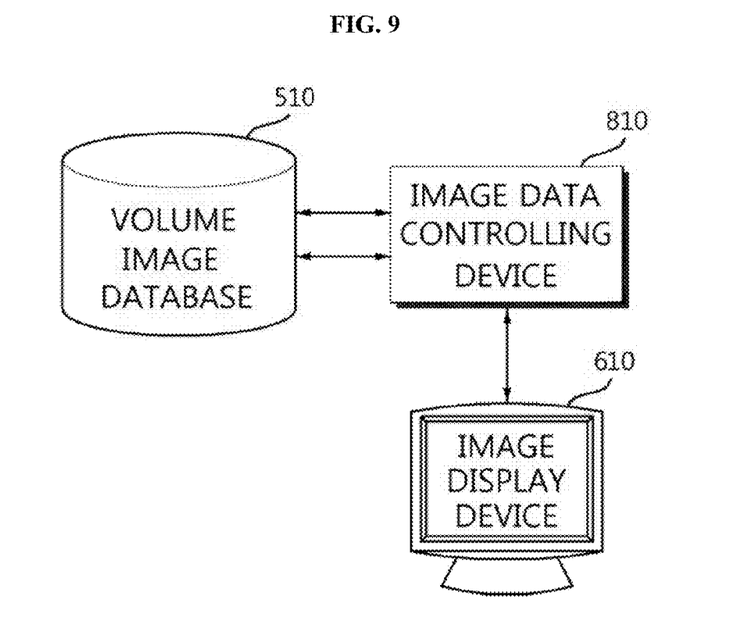
FIG. 9 is a schematic diagram of an apparatus for forming a panoramic X-ray image, according to an embodiment of the present invention.

FIG. 9 is a schematic block diagram of a panoramic X-ray image processing and displaying apparatus, according to an embodiment of the present invention.

The apparatus may include a volume image database 510 for storing volume image data in accordance with embodiments of the present invention, an image display device 610 for receiving and displaying at least a piece of the image data stored in the volume image database 510, and an image data controlling device 810 for changing image data. The volume image database 510 may also be referred to as an image data storage, and the image data controlling device 810 as an image processing unit.

The volume image database 510 may store and manage pieces of volume image data that refer to a set of pieces of image data for multiple image layers, as shown in FIGS. 7 and 8.

The image display device 610 may display image data input from the image data controlling device 810.

Figure 10:
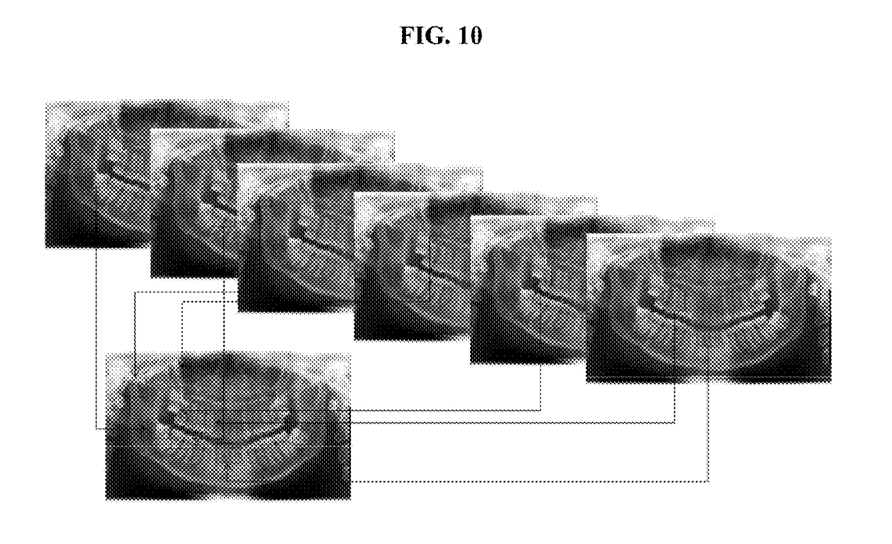
FIG. 10 is a conceptual view showing an example of forming a panoramic X-ray image, according to an embodiment of the present invention.

Upon request for panoramic image reconstruction from a user input (not shown), the image data controlling device 810 may set a reference image layer from among multiple image layers and designate at least one block in the reference image layer. FIG. 10 shows an exemplary panoramic image (on the lower left side) of the reference image layer set from among 6 image layers with 8 blocks designated in the reference image layer. A subsequent process may be performed, including: i) finding blocks in other image layers, which correspond to a block of the reference image layer; and ii) selecting the clearest block by comparing image data, i.e., pixel data of the blocks. The process continues to iii) wherein replacement of the designated block in the reference image layer with the selected block is performed, if the selected block is not the block designated in the reference image layer. For all the blocks designated in the reference image layer, operations i) to iii) may be repeated until reconstruction of the reference image layer is completed. The image controlling device may store the reconstructed reference image layer in the volume image database 510.

If the user requests reconstruction of a panoramic image displayed in the image display device 610, the process shown in FIG. 10 is performed by the image data controlling device 810 and the reconstructed panoramic image is displayed in the image display device 610. In other words, the panoramic image of the reference layer and its blocks may not be displayed in the image display device 610.

The reference image layer may be selected from among the multiple image layers. Alternatively, the reference image layer may be obtained by dividing the multiple image layers into multiple sections, selecting a clearest image layer for each section, and combining selected image layers from the multiple sections. In this case, after combination of the clearest image layer for each area, comparison of pixel data for each block is done. Accordingly, the panoramic image is reconstructed with the clearest pixel data for each block, thereby improving visibility of the image.

The block may be designated by the user. Once the locations of multiple blocks are designated by the user through a user input unit (not shown), such as a mouse, a touch pad, a touch screen, etc., on the panoramic image being displayed in the image display device 610, the image data controlling device 810 performs the aforementioned operations i) to iii) based on the designated locations of the blocks. The locations and number of the blocks may be stored in the volume image database 510 in advance.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention may be applied to any program for showing a panoramic image, such as an image viewer used in diagnosis and a program used in image capturing, showing changed images and enabling adjustment. Furthermore, according to the present invention, a viewer for storing images and changing trajectories using multiple images is provided, enabling image layers to be freely shifted after being captured.

The invention claimed is:

1. An apparatus for reconstructing a panoramic X-ray image, the apparatus comprising:
    memory configured to store image data of multiple image layers detected by and received from a predetermined X ray detector through a predetermined communication link;
    at least one processor configured to perform at least one of determining a reference image layer among the multiple image layers, finding blocks that correspond to at least one block designated in the reference image layer from other image layers, selecting a block having a higher frequency in a predetermined frequency band, as a clearest block, from the found blocks by comparing frequencies in the predetermined frequency band of image data of the found blocks, and reconstructing the reference image layer by replacing the designated block in the reference image layer with the selected block as the clearest block in any of the other image layers, if the selected block is not the same as the designated block in the reference image layer;
    a display unit configured to display a panoramic image of the reconstructed reference image layer and
    a user input unit configured to receive an input signal for designating locations and the number of the blocks.

2. The apparatus of claim 1, wherein the reference image layer is selected from among the multiple image layers.

3. The apparatus of claim 2, wherein the reference image layer is obtained by dividing the multiple image layers into multiple regions, selecting the clearest image layer for each region, and combining selected image layers from the multiple regions.

4. The apparatus of claim 2, wherein the storage unit stores location information of the block in advance.

5. The apparatus of claim 2, further comprising: a user input unit for designating locations and the number of the blocks.

6. The apparatus of claim 1, wherein the reference image layer is obtained by dividing the multiple image layers into multiple regions, selecting the clearest image layer for each region, and combining selected image layers from the multiple regions.

7. The apparatus of claim 1, wherein the storage unit stores location information of the block in advance.

8. A method for reconstructing a panoramic X-ray image, the method comprising:
    storing, by a memory, image data of multiple image layers that are detected by and received from a predetermined x-ray detector through a communication link;
    determining, by at least one processor, a reference image layer among the multiple image layers stored in the memory;
    finding, by the at least one processor, blocks that correspond to at least one block designated in the reference image layer from other image layers;
    selecting, by the at least one processor, a block having a higher frequency in a predetermined frequency band from the found bocks as a clearest block by comparing frequencies in the predetermined frequency band of image data of the found blocks;
    reconstructing, by the at least one processor, the reference image layer by replacing the designated block in the reference image layer with the selected block as the clearest block in any of the other image layers, if the selected block is not the same as the designated block in the reference image layer; and after determining the reference image layer among the multiple image layers, receiving, by a user input unit, locations and the number of the blocks from a user.

9. The method of claim 8, wherein the reference image layer is selected from among the multiple image layers.

10. The method of claim 9, wherein the reference image layer is obtained by dividing the multiple image layers into multiple regions, selecting the clearest image layer for each region, and combining selected image layers from the multiple regions.

11. The method of claim 9, further comprising:

after determining the reference image layer among the multiple image layers, receiving locations and the number of the blocks from a user.

12. The method of claim 8, wherein the reference image layer is obtained by dividing the multiple image layers into multiple regions, selecting the clearest image layer for each region, and combining selected image layers from the multiple regions.

13. The method of claim 8, further comprising:

before finding blocks that correspond to at least one block designated in the reference image layer from other image layers, designating the block with pre-stored location information.

14. The method of claim 13, further comprising:

before finding blocks that correspond to at least one block designated in the reference image layer from other image layers, designating the block with pre-stored location information.

* * * * *